(12) United States Patent
Nohammer et al.

(10) Patent No.: US 8,043,563 B2
(45) Date of Patent: Oct. 25, 2011

(54) ELECTRONIC BIOSENSOR ARRANGEMENT

(75) Inventors: Christa Nohammer, Vienna (AT); Daniel Paulo Wiese Meneses Rocha, Queijas (PT); Caspar Van Vroonhoven, EJ Den Haag (NL); Michael Johannes Vellekoop, Hinterbruhl (AT)

(73) Assignee: Austrian Research Centers GmbH-ARC, Vienna (AT)

( * ) Notice: Subject to any disclaimer, the term of this patent is extended or adjusted under 35 U.S.C. 154(b) by 279 days.

(21) Appl. No.: 12/300,978

(22) PCT Filed: May 15, 2007

(86) PCT No.: PCT/AT2007/000233
§ 371 (c)(1),
(2), (4) Date: Nov. 14, 2008

(87) PCT Pub. No.: WO2007/131255
PCT Pub. Date: Nov. 22, 2007

(65) Prior Publication Data
US 2009/0206847 A1 Aug. 20, 2009

(30) Foreign Application Priority Data
May 15, 2006 (AT) .................. A 830/2006

(51) Int. Cl.
*G01N 27/00* (2006.01)
(52) U.S. Cl. ....... 422/82.01; 422/50; 422/68.1; 435/7.1; 435/283.1
(58) Field of Classification Search .................. 341/126, 341/155; 435/7.1, 283.1; 436/518; 422/50, 422/68.1, 82.01
See application file for complete search history.

(56) References Cited

U.S. PATENT DOCUMENTS
4,860,232 A * 8/1989 Lee et al. ...................... 702/104
(Continued)

FOREIGN PATENT DOCUMENTS
WO WO 2004/057022 7/2004
(Continued)

OTHER PUBLICATIONS
International Search Report, issued in Int. App. No. PCT/AT2007/000233, mail date Aug. 10, 2007.
(Continued)

*Primary Examiner* — Melanie J Yu
(74) *Attorney, Agent, or Firm* — Fulbright & Jaworski L.L.P.

(57) ABSTRACT

An electronic biosensor arrangement (1), comprising a receiving region (2) for biological material, a sensor-electrode arrangement (3) with sensor electrodes (3a, 3b) which intermesh in a comb-like manner being associated therewith, with which sensor electrodes (3a, 3b) a measuring circuit (5) is connectable for measuring an electrical measurement parameter on the sensor electrodes (3a, 3b) and influenced by biological material, wherein the sensor electrodes (3a, 3b) form a plurality of sensor capacitors ($C_{sensor,1}$ to $C_{sensor,N}$), with which electronic switching means ($S_{2,1}$ to $S_{2,N}$) driven by a control logic (8) are associated for connecting to earth or to a voltage source carrying a measurement voltage ($V_{drive}$), respectively, comprising a reference capacitor ($C_{ref}$), to which a switching means ($S_1$) driven by the control logic (8) and arranged for optionally connecting to earth or to the measurement voltage ($V_{drive}$) is likewise assigned, wherein the capacitors ($C_{ref}$, $C_{sensor1}$–$C_{sensor,N}$) are also combined to a node (A), which is connected to an input (−) of a differential amplifier (10), and with which measurement capacitors ($C_0$ to $C_5$) having binary-weighted capacities ($C_{min}$ to $32C_{min}$) are furthermore connected for forming an SAR comparison unit, with the measurement capacitors being also selectively connectable via switching means ($S_{3,0}$ to $S_{3,5}$) driven by the control logic (8) to a voltage source ($V_{array}$) or to earth for the purpose of providing charge-difference for SAR conversion.

5 Claims, 4 Drawing Sheets

U.S. PATENT DOCUMENTS

| | | | |
|---|---|---|---|
| 5,027,814 A * | 7/1991 | Carroll et al. | 607/5 |
| 5,235,333 A * | 8/1993 | Naylor et al. | 341/118 |
| 5,920,275 A * | 7/1999 | Hester | 341/172 |
| 6,686,865 B2 * | 2/2004 | Confalonieri et al. | 341/172 |
| 7,413,859 B2 * | 8/2008 | Paulus et al. | 435/6 |
| 7,756,560 B2 * | 7/2010 | Frey et al. | 600/345 |
| 2001/0017383 A1 * | 8/2001 | Yach et al. | 257/296 |
| 2003/0160714 A1 * | 8/2003 | Yoshinaga | 341/122 |
| 2003/0226768 A1 | 12/2003 | Hoffman et al. | 435/6 |
| 2003/0234736 A1 * | 12/2003 | Tachibana et al. | 341/172 |
| 2005/0068046 A1 * | 3/2005 | Frey et al. | 324/686 |

FOREIGN PATENT DOCUMENTS

| | | |
|---|---|---|
| WO | WO 2005/001479 | 1/2005 |
| WO | WO 2006/029591 | 3/2006 |

OTHER PUBLICATIONS

Kung et al., "A digital readout technique for capacitive sensor applications," *IEEE J. of Solid-state Circuits*, 23 (4): 972-977, 1988.

Kung et al., "Digital Cancellation of noise and offset for capacitive sensors," IEEE Transactions on Instrumentation and Measurement, 42 (5): 939-942, 1993.

Laureyn et al., "Nanoscaled interdigitated titanium electrodes for impedimetric biosensing," *Sensors and Actuators B.*, 68 (1-3): 360-370, 2000.

Schienle et al., "12.2—A fully electronic DNA sensor with 128 positions and in-pixel A/D conversion," *Digest of Technical Papers*, 220-229, 2004.

Van Vroonhoven et al., "A readout circuit for capcitive biosensors with integrated SAR A/D conversions," *Circuits and Systems*, 1418-1421, 2006.

* cited by examiner

ELECTRONIC BIOSENSOR ARRANGEMENT

This application is a national phase application under 35 U.S.C.§371 of International Application No. PCT/AT2007/000233 filed 15 May 2007, which claims priority to Austrian Application No. A 830/2006 filed 15 May 2006. The entire text of each of the above-referenced disclosures is specifically incorporated herein by reference without disclaimer.

The invention relates to an electronic biosensor arrangement, comprising a receiving region for biological material, a sensor-electrode arrangement with sensor electrodes which intermesh in a comb-like manner being associated therewith, to which sensor electrodes a measuring circuit is connectable for measuring an electrical measurement parameter on the sensor electrodes and influenced by biological material.

Such a biosensor arrangement is known, e.g., from the article written by E. Laureyn et al., "Nanoscaled interdigitated titanium electrodes for impedimetric biosensing", Sensors and Actuators B, vol. 68 (2000), pp 360-370. Here, the object is to detect affinity-based interactions between complementary molecules, wherein a binding of target molecules to selective probe coatings is caused in the electric properties in the region of the electrodes intermeshing in a comb-like manner. These changes may be detected as an impedance shift, thus obtaining a direct electric signal referred to the affinity binding. In this manner, e.g., the immobilization of the glucose oxidase can be monitored using impedance spectroscopy.

For biological purposes it is often sufficient to distinguish simply between the states of binding and non-binding. Usually, the reactions, which occur when, e.g., a DNA or a different specific material (depending on the application) binds to receptors on the electrodes, are slow, taking several seconds, as a rule. It involves relatively great efforts to monitor such biological reaction processes by means of the known biosensor arrangement, wherein the expenditures on equipment required for monitoring a plurality of such reaction processes are also high.

Studies have shown that there will be a 20% magnitude change in the dielectric constant of a primarily aqueous solution, which is present between the electrodes, during a reaction process, e.g. when a DNA or a different biological material, depending on the application, is being bound to receptors on the electrodes, with water (having a relatively high dielectric constant) being displaced by reactants with a low dielectric constant; this means that the capacity between two electrodes of such a capacitive biosensor formed by a pair of electrodes may be reduced to be as low as about 80% of the initial capacity value. Therefore, such capacity values and changes in the capacity values should be detected, it being desirable to monitor a large number of reaction processes and, thus, biosensors at the same time, and the efforts involved in measurement need nevertheless be kept low.

Thus, it is an object of the invention to propose a biosensor arrangement as initially described, by means of which a large number of biological reaction processes can be monitored at the same time, with e.g. 10,000 simultaneous processes being definitely conceivable, and wherein the expenditure on equipment necessary shall be kept low.

In this context, the invention is based on the finding that the usually used on-chip-analyzing systems for biochemistry offer the uncomplicated possibility of realizing individual biosensors in the mentioned large number on one chip and of reading these biosensors at a correspondingly high rate as regards a capacity decrease, wherein, basically, a principle known per se from other measurement applications, i.e. the SAR technique (SAR—successive approximation registers), may furthermore be used for capacity measurement so as to quickly achieve a measurement result in digital form which is sufficiently accurate. This SAR technique is known, e.g., for use with acceleration sensors and pressure sensors, and it is based on measurements of capacity differences, cf., e.g., the article written by Joseph T. Kung et al., "Digital Cancellation of Noise and Offset for Capacitive Sensors", Transactions on Instrumentation and Measurement, vol 42, no 5, October 1993, pp 939-942. This SAR technique known per se may be advantageously used within the scope of the present biosensor arrangement in a modified form with numerous biosensors.

Accordingly, the invention provides for an electric biosensor arrangement as defined in the enclosed claim 1. Advantageous embodiments and further developments are set out in the dependent claims.

With the inventive biosensor arrangement, the individual sensor capacitors formed by the respective sensor electrodes, i.e. biosensors, are one by one connected to the measurement voltage and "read", wherein a SAR approximation is carried out for each reading, i.e. for each measurement-value detection, wherein, at a correspondingly higher rate, the individual measurement capacitors, starting with the measurement capacitor of the highest value in the output of the digital measurement results in correspondence with the bit of the highest value, will be connected and will be switched off as a function of the respective result of difference, or will remain connected when the measurement capacitor of the next-lowest value will subsequently be connected. This successive approximation finally provides a digital signal which indicates the capacity difference between the reference capacitor and the respective sensor capacitor at a predefined resolution, in correspondence with the smallest measurement capacitor. Thus, the capacity value of the respective sensor capacitor will be obtained by subtracting said capacity difference from the capacity value of the reference capacitor. However, for further data processing, already the value of capacity difference is often sufficient which will be obtained immediately in digital form and may thus be immediately further processed.

While the one input of the differential amplifier, in particular the inverting input (−) is supplied with the net voltage given by the total charges on the respective capacitors, the other input, i.e. the non-inverting input (+), may be preferably connected to earth, yet with an offset voltage possibly occurring. To provide remedy in this context, it is advantageous if the differential amplifier has a feedback branch extending from its output to the one input, wherein a switch controlled by the control logic is arranged in said feedback branch for closing and opening the latter, and wherein the differential amplifier acts as a comparator during the SAR approximation phase when the feedback branch is open, whereas when the feedback branch is closed, the differential amplifier, during an initializing phase feedbacks an amplifier-offset voltage to the node for the subsequent compensation. Here, for reasons of a safe measurement, it is advantageously further provided that after the initializing phase the switch provided in the feedback branch will be driven by the control logic either simultaneously with the switching of the switching means assigned to the reference capacitor or directly before said switching means will be switched so as to connect the reference capacitor to earth rather than to measurement voltage.

Likewise, it is also of advantage if a resistance is connected upstream of the one input of the differential amplifier for frequency damping in connection with an input capacity of the differential amplifier during the initializing phase.

Similarly to the sensor capacitors, the reference capacitor may be formed on the common chip, yet, the reference capacitor will be kept free of biological material, i.e. no reaction process will take place in its region so that there will be no change in its capacity value either. As to a structure which is particularly simple then as well as to a simple detection of measurement results, it is beneficial if the capacity value of the reference capacitor is selected so as to equate to the highest-possible capacity value of the individual sensor capacitors, wherein the capacity values of the sensor capacitors will be reduced by reactions occurring in the biological material.

Besides, also the measurement capacitors may be realized on the same chip.

In the following, the invention will be explained in more detail by way of the preferred exemplary embodiment illustrated in the drawings, yet without being restricted thereto. In detail:

FIG. 1 schematically shows an electronic biosensor arrangement according to the invention, including a following data-processing unit;

Figure 1:
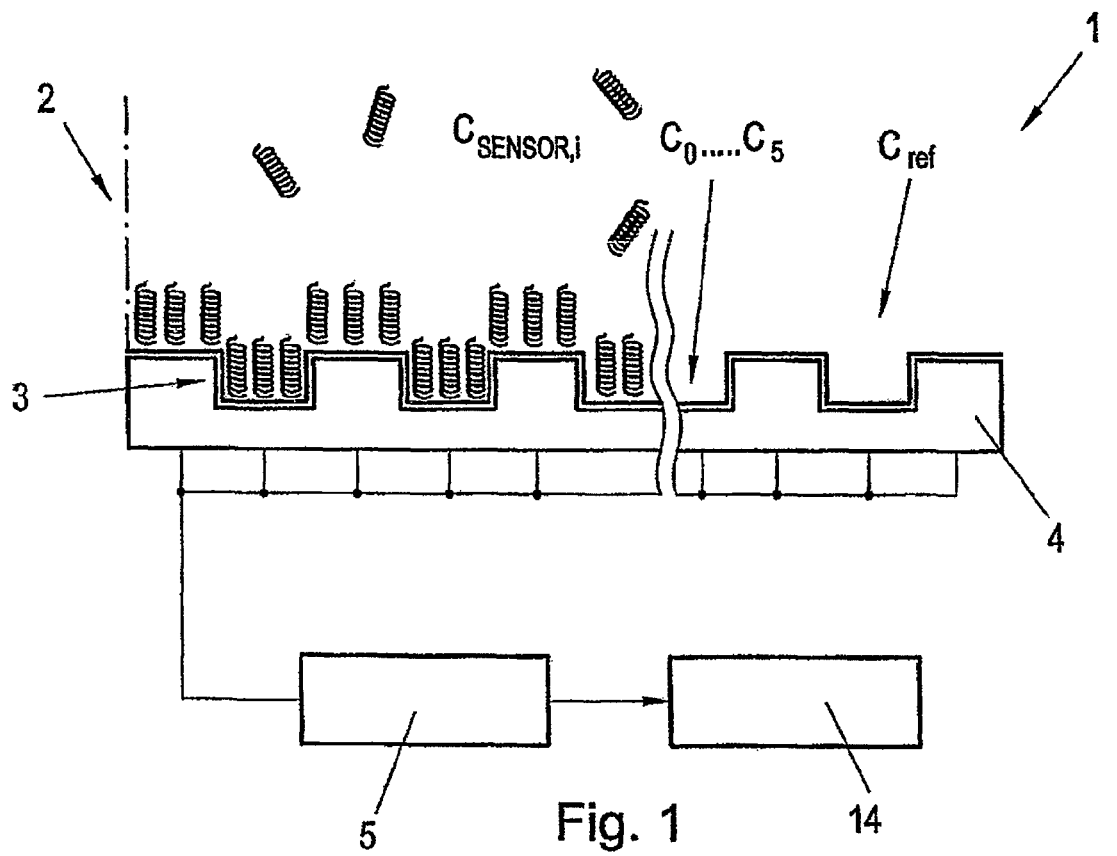

In FIG. 1, the basic principle of the present electronic biosensor arrangement 1 is schematically illustrated, wherein a sensor-electrode arrangement 3 is provided on a common chip 4 in a receiving region 2 (only very schematically indicated) for receiving biological material; outside of the receiving region 2 for the biological material, the sensor-electrode arrangement 3 furthermore provides a reference capacitor $C_{ref}$ and measurement capacitors $C_0$ to $C_5$. In the receiving region 2 for the biological material a number (e.g. 10,000) of sensor capacitors $C_{sensor,i}$, wherein i=1, 2, 3 ... N, is defined.

Figure 2B:
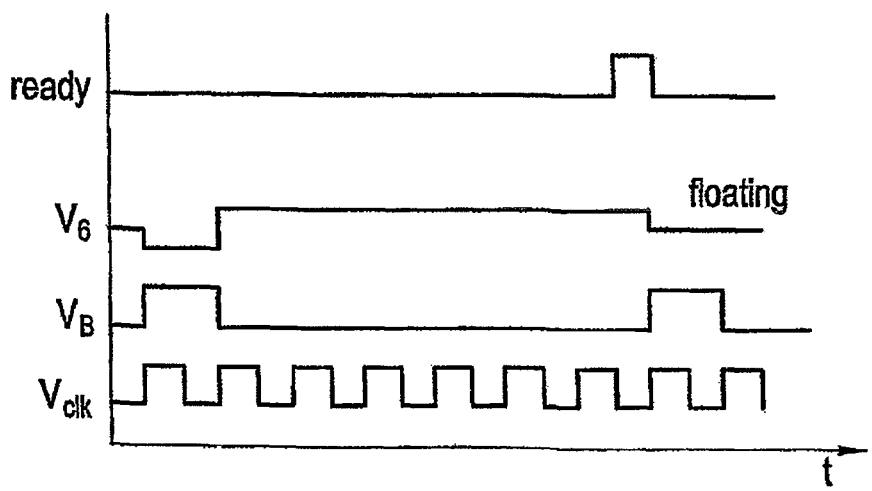
FIG. 2B shows a diagram of some of the voltage signals occurring in the circuit operation according to FIG. 2.
Figure 2A:
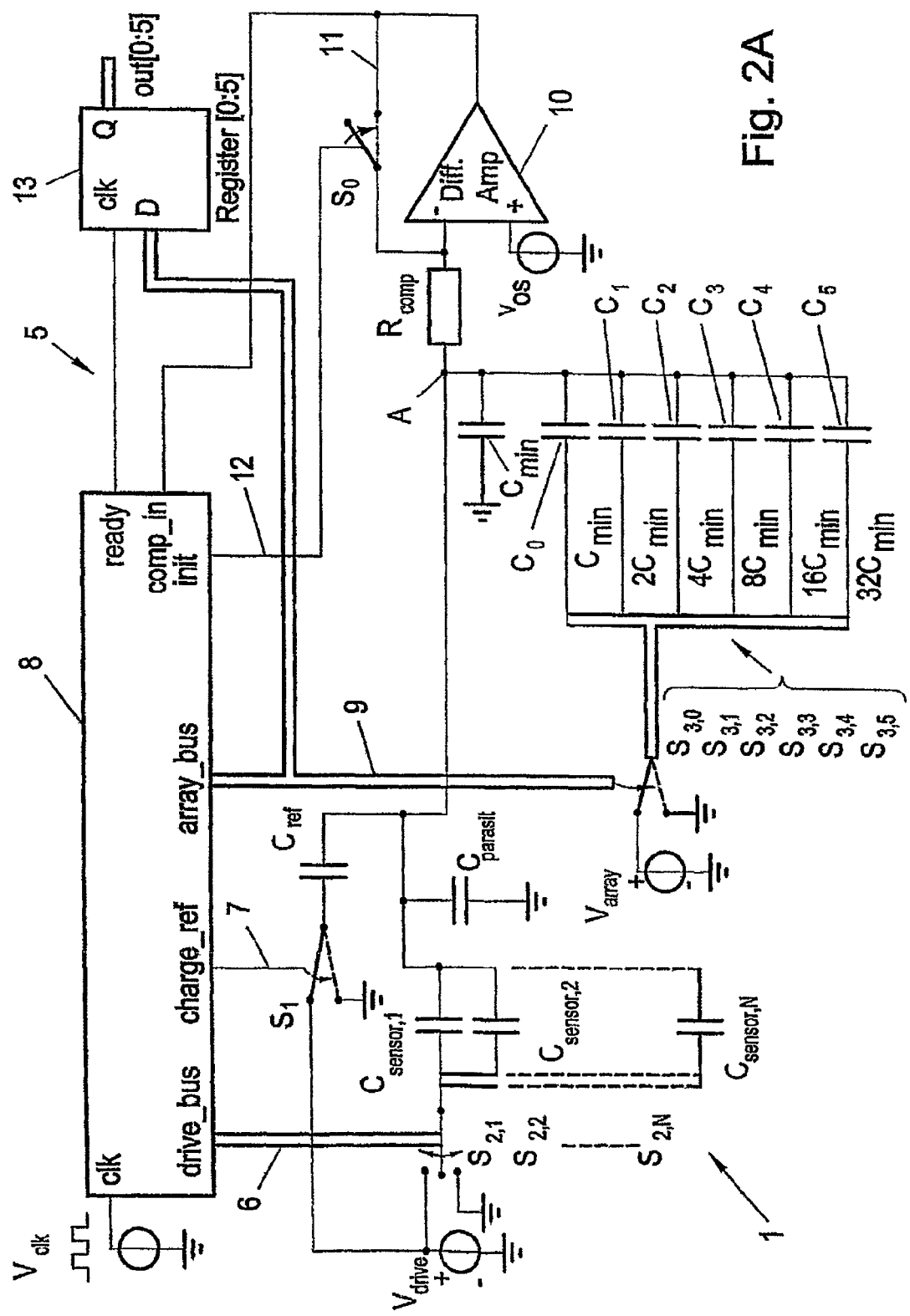
FIG. 2A shows a schematic circuit diagram of the individual biosensors and sensor capacitors with the measuring circuit assigned thereto.
Figure 3A:
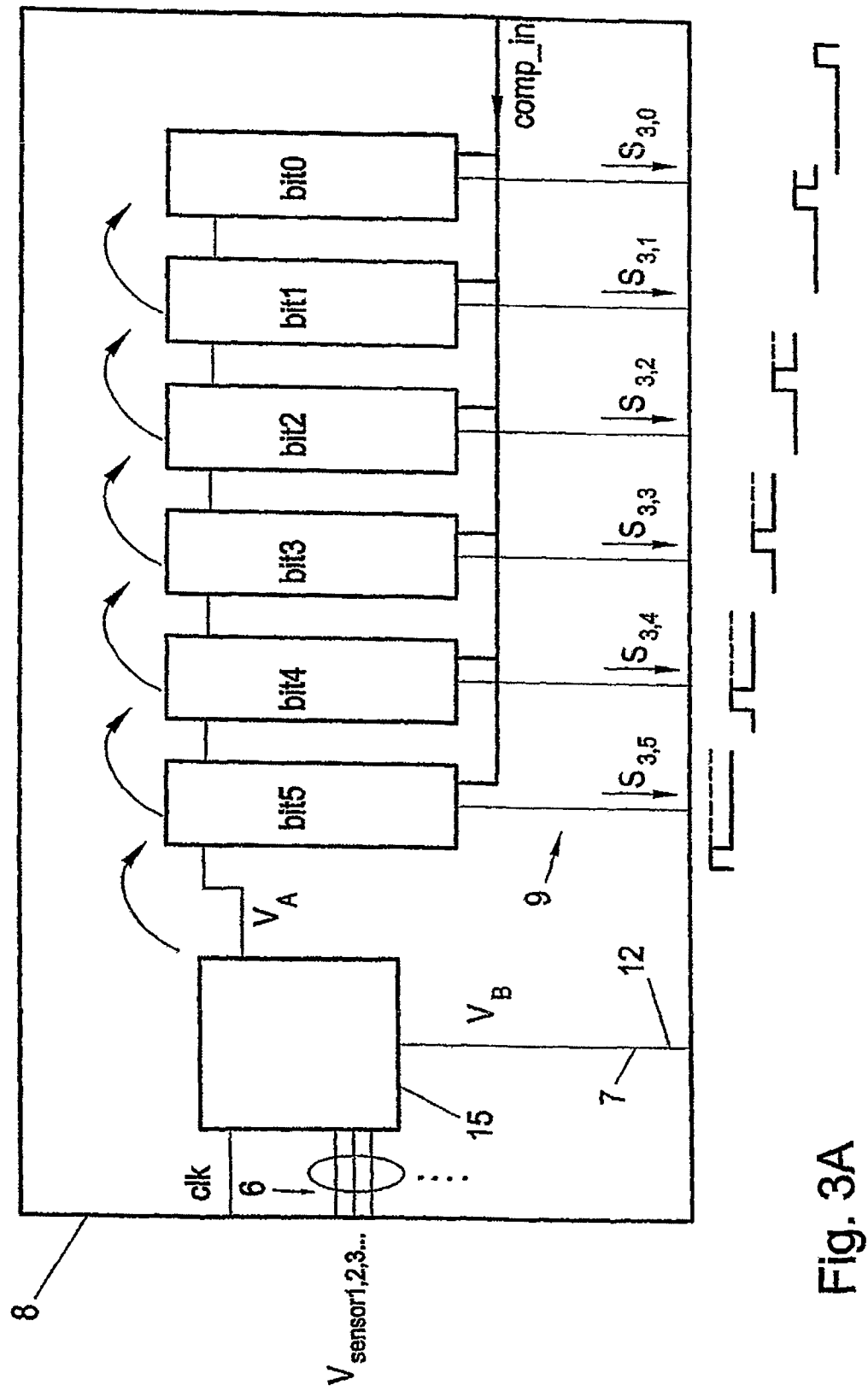
FIG. 3A shows a schematic circuit diagram of the control logic of the measuring circuit according to FIG. 2A.
Figure 3B:
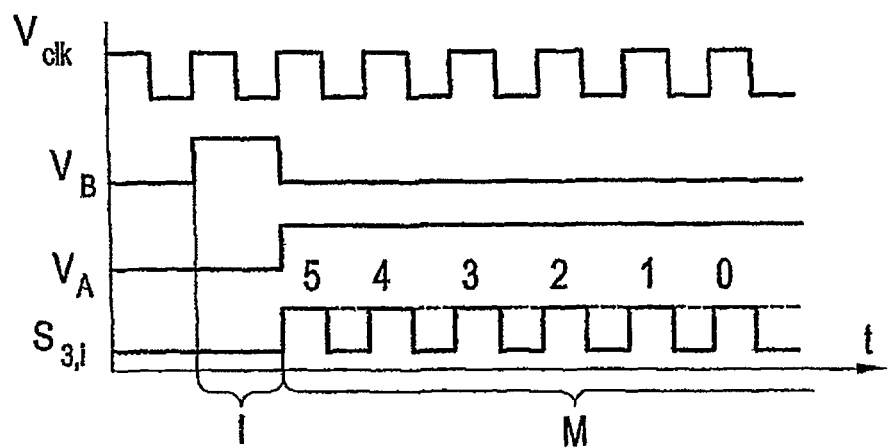
FIG. 3B shows different pulse signals of said control logic.
Figure 3C:
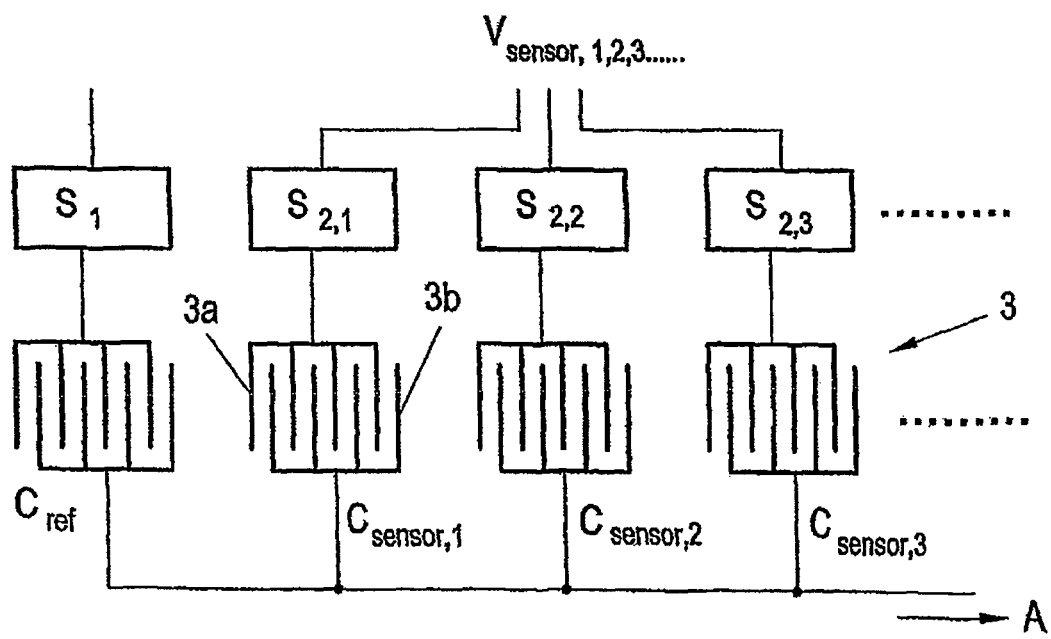
FIG. 3C shows, in a schematic representation, a number of biosensors comprised of sensor electrodes, including switching means assigned thereto, wherein also the reference capacitor comprised of comparable electrodes is shown with switching means assigned thereto.

Here, the individual sensor capacitors $C_{sensor,i}$ as well as the reference capacitor $C_{ref}$ (and likewise the measuring capacitors $C_0$ to $C_5$) are formed by electrodes intermeshing in a comb-like manner, as can be schematically seen from FIG. 3C. These capacitors $C_{ref}$ and/or $C_{sensor,i}$ are assigned to switching means $S_1$, $S_{2,1}$, $S_{2,2}$, ... $S_{2,i}$ ... $S_{2,N}$, and $S_{3,0}$, $S_{3,1}$ ... $S_{3,5}$, respectively, which may be seen from FIGS. 2A and 3C, and which are specifically formed by electronic switching means, e.g., directly in the region of the semiconductor chip 4, with a bus leading to the individual switching means $S_1$ to $S_3$ of the measuring circuit 5 for control purposes. The switching means $S_1$, $S_{2,i}$ and $S_{3,0}$ to $S_{3,5}$ are driven by a control logic 8 of the measuring circuit 5, wherein the switching means $S_1$ and $S_2$, depending on the respective measurement phase, in operation, establish an electric connection to a measurement voltage $V_{drive}$ or to earth, but they may optionally also remain floating (with the latter case relating to the switches $S_{2,i}$ for the biosensors, i.e. for the sensor capacitors $C_{sensor,i}$). The switching means $S_{2,i}$ (wherein i=1 ... N) and $S_1$ are driven via a control bus 6 and a control line 7, cf. FIG. 2A. A further control bus 9 of the control logic 8 leads to the switching means $S_{3,0}$ to $S_{3,5}$, which selectively connect the binary-weighted measurement capacitors $C_0$ to $C_5$ to a voltage source $V_{array}$ or to earth. The other side of the measurement capacitors $C_0$ to $C_5$ leads to a node A, to which also the reference capacitor $C_{ref}$ as well as the sensor capacitors $C_{sensor,i}$ are connected. This node A is connected to the one input, i.e. the inverted input (−), of a differential amplifier 10 via a resistance $R_{comp}$, with the other, non-inverted input (+) thereof being connected to earth, wherein FIG. 2A additionally shows in a schematic fashion that an offset voltage $V_{os}$ may possibly occur during operation. To be able to compensate for this offset voltage $V_{os}$ after an initializing phase I (cf. FIG. 3B), the differential amplifier 10 has a feedback branch 11 including a switch $S_0$. This electronic switch $S_0$ is again driven by the control logic 8 via a control line 12, this taking place in said initializing phase I prior to the measurement and approximation phase proper, which constitutes a phase of successive approximation, wherein this measurement phase M for one of the sensor capacitors $C_{sensor,i}$ as well as the initializing phase I are illustrated in FIG. 3B.

For the sake of completeness, in the circuit according to FIG. 2A, also a parasitic capacity present in chip 4 (cf. FIG. 1) is illustrated by a capacitor ($C_{parasit}$). Furthermore, a register 13 is shown which is provided for storing the bit order per sensor capacitor $C_{sensor,i}$, which forms the measurement result, wherein said measurement results will then be received by a data-processing unit 14 (cf. FIG. 1) for further processing.

The register 13 is indexed for each sensor capacitor, cf. the pulse signal "ready" in FIGS. 2A and 2B, wherein said pulses are used as clock pulses for the register 13. At an input D of the register 13, the switch signals are supplied which are provided for the switching means $S_{3,0}$ to $S_{3,5}$ and depend on the comparison of potentials of the measurement capacitors $C_0$ to $C_5$ with the respective sensor capacitor $C_{sensor,i}$ wherein this dependency manifests itself in the output signal (comp_in) of the differential amplifier 10, said output signal being supplied at the respectively designated input comp_in of the control logic 8.

Furthermore, FIG. 2B illustrates a control signal $V_b$ applied to the switching means $S_1$, and a control signal $V_6$ applied to the switching means $S_{2,i}$, as well as a clock signal $V_{clk}$. Here, it follows that the switching means $S_{2,i}$ may also remain floating, with the exception of the specific switching means for the currently measured sensor capacitor $C_{sensor,i}$, as will be explained in more detail below.

FIG. 3A shows the control bus 6 with individual lines for individual switch signals $V_{sensor1,2,3}$ ..., for the individual sensor capacitors $C_{sensor,1}$ ..., in more detail. These switch signals, as well as the switch signal $V_B$ supplied for the switching means $S_1$ for the reference capacitor $C_{ref}$ via the control line 7, and a further switch signal for the individual bit stages bit5, bit4, bit3, bit2, bit1 and bit0 in correspondence to the measurement capacitors $C_5$, $C_4$, ... $C_1$, $C_0$, are generated by an initializing and sensor-selecting circuit 15 within the control logic 8. The individual bit stages bit0 to bit5 are supplied with the output signal of the differential amplifier 10, i.e. the signal comp_in, so as to logically combine the same with the pulse signal $V_A$, cf. also FIG. 3B, with the result thereof being used for generating the control signals (on the bus 9, indicated by arrows) for the switching means $S_{3,5}$, $S_{3,4}$ ... $S_{3,0}$ assigned to the measurement capacitors $C_5$, $C_4$ ... $C_0$. In FIG. 3A, these control signals are shown directly below the individual outputs to the individual switching means $S_{3,5}$ etc.; here, the horizontal dotted line also indicates that the control signal may also remain high, as a function of the signal output and the output of the differential amplifier, i.e. as a function of the result of the comparison currently being made, as will be explained in further detail below.

FIG. 3B shows in combination the individual pulse signals $V_{clk}$ (clocked signal), $V_B$ (control signal for the switching means $S_1$ on the control line 7, as well as to the switch $S_0$ on the control line 12), $V_A$ (pulse signal to the bit stages bit5 to bit0) as well as the individual switch signals $S_{3,i}$, wherein, as regards the initializing phase I preceding the measurement phase M proper, it is illustrated that the reference capacitor $C_{ref}$ is applied to the measurement voltage $V_{drive}$ according to the signal $V_B$, and also that the feedback branch 11 of the differential amplifier 10 is closed by the switch $S_0$, whereas the switching means $S_{3,0}$ to $S_{3,5}$ assigned to the measurement capacitors $C_0$ to $C_5$ are connected to earth.

In detail, as regards the pulse signals described, it shall be additionally mentioned that the clock signal $V_{clk}$ is assumed to trigger all respective processes with its rising edges. However, the sampling of the output signal comp_in of the differential amplifier 10 is effected in case of a rising edge of the inverted clock signal, i.e. after the respective bit has had a half period of time for charging. As mentioned above, the outputs of the bit stages bit5 to bit0 constitute the control signals for the switching means $S_{3,5}$, ... $S_{3,0}$, which are also referred to as SAR switches (SAR—successive approximation register). As mentioned above, in FIG. 3A, these switch signals are shown below the bit stages bit5 to bit0, wherein it is also illustrated that they rise successively. The possibility of keeping the signal in the high state, as is illustrated in dotted lines, will result if the respective approximation sum at the input of the comparator, i.e. at the input (−) of the differential amplifier 10, is negative.

The signal $V_A$ triggers the measurement and approximation phase proper. When the reference capacitor $C_{ref}$ has been charged, with all measurement capacitors $C_5$ to $C_0$ having to be connected to earth during said charging time (initializing phase I), this signal $V_A$, when rising, triggers the output of the first array bit, the MSB bit, in the present case the bit no. 5. Here, it should be mentioned that a design with six bits serves as an example and reflects a good compromise between the number of weighted capacitors $C_0$, $C_1$, ... and the limit of detection. Certainly, also more (or less) measurement capacitors, e.g. 12 measurement capacitors C, may be provided.

During the initializing phase I the signal $V_B$ is high prior to the measurement proper and urges the switching means $S_1$ for the reference capacitor $C_{ref}$ into its closed state. Likewise, the signal $V_B$ causes the switch $S_0$ to close in the feedback branch 11 of the differential amplifier 10 so as to ensure a uniform feedback during this phase. The number of clock periods during which the signal $V_B$ is high depends on the decay time necessary after the approximation phase.

The output signal comp_in of the differential amplifier 10 is of interest when the latter acts as a comparator, i.e. during the measurement or approximation phase proper. The signal comp_in will be positive if the total sum of measurement capacities switched on is higher at the respective point of time than the absolute capacity difference between the sensor capacitor $C_{sensor,i}$ and the reference capacitor $C_{ref}$. However, the signal comp_in will be negative if several measurement capacitors have to be switched on. It is assumed that this output signal comp_in of the differential amplifier will be rising quickly enough after a respective bit (on the bus 9) has been switched on. This is why attention has to be paid to a quick mode of operation of the differential amplifier 10.

The circuit described allows for sampling rates of up to 15 mega samples per second to be reached at low resolutions, wherein the circuit with the SAR converter 16, which has been realized by the measurement capacitors $C_0$ to $C_5$ as well as by a starting capacitor $C_{min}$ including the control logic 8 assigned thereto and the differential amplifier or comparator 10, may be implemented with an extraordinary compact circuit with low power input.

During operation, the sensor capacitors $C_{sensor,1}$ ... $C_{sensor,n}$ are multiplexed, wherein, for determining one of these sensor capacitors, $C_{sensor,i}$, the measurement capacitors $C_n$, with n=0 to 5, are connected one after the other so as to perform SAR algorithm. All these capacitors are connected to the node A which is located above the resistance $R_{comp}$ at the (−)-input of the differential amplifier 10 and has a high impedance when the feedback branch 11 is open, i.e. when the switch $S_4$ is opened. A single sensor capacitor is selected from a number of sensor capacitors for each measurement circuit, and those which are currently not being measured remain floating.

If the biosensor arrangement is activated during operation, the whole digital logic plus switch-driving means will be initialized; at this point of time there will be no measurement yet, and there will be no information available at the output. In this situation the individual switches have the following states:

| | |
|---|---|
| $S_0$ | open |
| $S_1$ | connected to earth |
| $S_{2,all}$ | floating |
| $S_{3,all}$ | connected to earth |

Then, the measurement of the first sensor capacitor, e.g. $C_{sensor,1}$, will be started. As mentioned above, two phases each are provided, i.e. the initializing phase I during which the reference capacitor $C_{ref}$ having a fixed capacity value is charged, and the measurement phase M proper during which the respective sensor capacitor $C_{sensor,i}$ is being switched on; thereafter, the measurement capacitors $C_5$ to $C_0$ will be connected in the SAR array. The positions of the switches for the initializing phase during measurement, e.g. of the sensor capacitor $C_{sensor,1}$, are as follows:

| | |
|---|---|
| $S_0$ | closed |
| $S_1$ | connected to $V_{drive}$ |
| $S_{2,1}$ | connected to earth |
| $S_{2,x/\{1\}}$ | floating |
| $S_{3,x}$ | connected to earth |

The addition "x" indicates that in each case all switches are involved, whereas the addition "/{1}" indicates that all switches $S_2$ are floating, except the switch for the first sensor capacitor $C_{sensor,1}$.

During the measurement phase M proper the states of the individual switches are as follows:

| | |
|---|---|
| $S_0$ | open |
| $S_1$ | connected to earth |
| $S_{2,1}$ | connected to $V_{drive}$ |
| $S_{2,x/\{1\}}$ | floating |

$S_{3,n\ (n=5,4,\ldots 0)}$ these switches $S_{3,n}$ are actuated one after the other and optionally kept connected, depending on the output comp_in of the comparator, as already mentioned above, cf. also the switch or control signals below the control logic 8 in FIG. 3A.

As mentioned above, during the initializing phase I the feedback switch $S_0$ is closed and the reference capacitor $C_{ref}$ is connected to the measurement voltage $V_{drive}$, while at least the first sensor capacitor $C_{sensor,i}$ to be measured is connected to earth, as are the measurement capacitors $C_n$. The differential amplifier 10 virtually forces mass potential at its (−)-input. During this phase the resistance $R_{comp}$ serves for achieving a phantom-zero frequency compensation in combination with an input capacity. During the measurement phase or approximation phase M following thereupon the resistance $R_{comp}$ will have practically no effect since the current flowing through the same will be negligible.

During this approximation or measurement phase M the amplification is high at the operation frequency of the differential amplifier 10 so as to amplify the smallest input voltages during the last step of the approximation to a logic "high" or "low". The smaller the sensor capacitors to be measured, the higher the amplification of the amplifier or comparator 10 has to be.

During this measurement phase M one sensor capacitor after the other is connected to the measurement voltage $V_{drive}$, wherein the voltage at the node A will then become proportional to the capacity difference. The algorithm of the successive approximation is used for converging to a digital measurement signal representing said capacity difference. To this end, as mentioned above, the measurement capacitors are connected to the voltage $V_{array}$, starting with the capacitor $C_5$ of the highest capacity value (32 $C_{min}$), and are kept connected, if occasion arises. This depends on the resulting sign of the voltage in the node A.

In the following, this will be explained in more detail by way of a specific example: it is assumed that all sensor capacitors have a nominal value (without biological reaction) of about 10 pF. Furthermore, it is assumed that the first sensor capacitor $C_{sensor,1}$, influenced by a biological reaction, has decreased to a value of 8.58 pF. This change in the capacity is substantial enough to be representative for the process and may thus be detected.

The reference capacitor $C_{ref}$ is a capacitor on which no reaction takes place; its capacity value is 10 pF. Correspondingly to a binary order, the measurement capacitors $C_0$ to $C_5$ have the capacity values 50 fF, 100 fF, 200 fF, 400 fF, 800 fF and 1.6 pF. During measurement, the difference of the capacity of the sensor capacitor $C_{sensor,1}$ and the reference capacitor $C_{ref}$ will be stored at the node A. The charge will thus be equivalent to a capacity of 8.58 pF−10 pF=−1.42 pF. In the following, the measurement capacitors $C_5$ to $C_0$ will one after the other be connected to the voltage $V_{array}$, as described above, so as to find out whether the equivalent charge is positive or negative. In the present example, this results in the following table of values:

| $C_{5...0}$ | node A | equivalent remaining capacity | comp_in | binary output |
|---|---|---|---|---|
| 1.6 pF | −1.42 pF | +0.18 pF | negative | 0 |
| 800 fF | −1.42 pF | −0.62 pF | positive | 1 |
| 400 fF | −0.62 pF | −0.22 pF | positive | 1 |
| 200 fF | −0.22 pF | −0.02 pF | positive | 1 |
| 100 fF | −0.02 pF | +0.08 pF | negative | 0 |
| 50 fF | −0.02 pF | +0.03 pF | negative | 0 |

The following result will be obtained:
6-bit output: 011100; corresponding measurement result=8.6 pF (in this example, the resolution is 50 fF).

The measurement result of 8.6 pF results from the difference of the capacity of the reference capacitor (10 pF) minus the capacity measured (1.4 pF, corresponding to the 6-bit output 011100).

As mentioned above, the measurement capacitors $C_0$ to $C_5$ are preferably also realized on the chip 4 so as to achieve a particularly compact design of the whole biosensor arrangement 1.

In FIG. 2A, another capacitor $C_{min}$ is shown which is provided in parallel to the measurement capacitors $C_0$ to $C_5$ proper, which is always switched between the node A and earth and which is of no function for the sensor activity and only advantageous for a calibration and testing procedure prior to putting the sensor into operation. The capacitor $C_{min}$ may also be omitted.

If, during a measurement and as a function of the sign of the voltage at the node A, i.e. at the (−)-input of the differential amplifier 10, the respective measurement capacitor $C_n$ (wherein n=0 . . . 5, in the example shown) is either kept connected to the supply voltage $V_{array}$, thus contributing to the current approximation sum, or is connected to earth, thus being inactive for the further conversion, the switching means $S_{3,n}$ will be driven by the control logic 8, as above described, so as to implement the above modified SAR algorithm. During this conversion, the voltage V at the node A may generally be as follows:

$$V = \frac{(C_{sensor,i} - C_{ref})V_{drive} + C_{array}V_{array}}{C_{sensor,i} + C_{ref} + C_{parasit} + C_{array,TOT}}$$

In this relation, $C_{array,TOT}$ represents the total capacity of the measurement capacitor, whereas $C_{array}$ indicates the linear combination of those weighed measurement capacitors that represent the approximation until the just-described point. After the complete measurement circuit, on the bus 9 driving the switching means $S_{3,n}$ those bits are present in series that produce the capacity difference measured (in the present example: 1.4 pF).

The total capacity of the measurement capacitors, $C_{array,TOT}$, is determined by the number of bits N (in the present example, N=6), as it is desired for the accuracy of measurement and resolution, as well as by the smallest capacitor which can be realized using a certain technology in a manner still providing sufficient accuracy. The value of this total capacity is $C_{array,TOT}=2^{N+1} \cdot C_{min}$. If desired, the maximum possible difference, (absolute) value=$|C_{sensor,i}-C_{ref}|$, be adapted to the complete region of the SAR converter, i.e. according to $$V_{array} = \frac{|C_{sensor,i} - C_{ref}|}{2^{N+1}C_{min}} V_{drive}$$

As a consequence of the mode of two-phase operation, including the initializing phase I and the measurement phase M proper, the offset sensitivity of the arrangement can be substantially reduced. During the initializing phase I the offset of the differential amplifier 10 is stored in the node A and, then, it will be eliminated by the difference amplification during the approximation phase (measurement phase M). Assuming that the biosensor arrangement 1 is operated at high switching frequencies, the 1/f noise may be considered offset.

When the switch $S_0$ is being opened in the feedback branch 11, the charge is injected in the node A with high impedance so as to cause a small offset voltage in this node. This offset voltage can only be detected if it is present with a magnitude as is the voltage V at the node A, which occurs when the LSB capacitor (capacitor $C_0$) is being measured during the measurement phase. This may be the case if small biosensors are measured since $C_{array,TOT}$ will not change and the measurement voltage $V_{drive}$ has an upper limit as regards the supply voltage. If necessary, the offset voltage may also be compensated for in a digital manner by a calibration step.

The invention claimed is:

1. An electronic biosensor arrangement comprising a receiving region for biological material, a sensor-electrode arrangement with sensor electrodes which intermesh in a comb-like manner being associated therewith, a measuring circuit to which the sensor electrodes are connectable for measuring an electrical measurement parameter on the sensor electrodes and influenced by biological material during use, said biosensor arrangement further comprising a reference capacitor with which a first switch driven by a control logic and arranged for optionally connecting one side to earth or to a first voltage source carrying a measurement voltage is associated, wherein the sensor electrodes form a plurality of sensor capacitors, with which a first group of switches driven by the control logic during use are associated for selectively connecting one side of the sensor capacitors to the first voltage source, respectively, wherein other sides of the sensor capacitors are combined in a node, which is connected to a first input of a differential amplifier, wherein separate measurement capacitors having binary-weighted capacities are furthermore connected to the node for forming an SAR (Successive Approximation Register) comparison unit, with the measurement capacitors being also selectively connectable via a second group of switches driven by the control logic to a separate, second voltage source carrying a fixed voltage for the purpose of providing charge-difference for SAR conversion during use, wherein the control logic is arranged to:
drive the first switch to connect it to the first voltage source in an initializing phase;
to successively drive the first group of switches to successively connect the sensor capacitors to the first voltage source, so that respective differences of capacity of the respective sensor capacitor and the reference capacitor are stored at the node; and
to successively drive the second group of switches to connect the measurement capacitors to the second voltage source each time during which one of the sensor capacitors is connected to the first voltage source, to determine charge differences between the respective sensor capacitor and the successively connected measurement capacitor.

2. The biosensor arrangement of claim 1, wherein the differential amplifier has a feedback branch extending from its output to the first input, wherein a second switch driven by the control logic is arranged in said feedback branch for closing and opening the latter, and wherein the differential amplifier acts as a comparator during a SAR approximation phase when the feedback branch is opened during use, whereas when the feedback branch is closed, the differential amplifier, during the initializing phase, feedbacks an amplifier-offset voltage to the node for a subsequent compensation.

3. The biosensor arrangement of claim 2, wherein after the initializing phase, the second switch provided in the feedback branch will be driven by the control logic either simultaneously with the switching of the first switch associated with the reference capacitor or directly before the first switch will be switched so as to connect the reference capacitor to earth instead of to the measurement voltage during use.

4. The biosensor arrangement of claim 2, wherein a resistance is connected to the first input of the differential amplifier for frequency damping in connection with an input capacity of the differential amplifier during the initializing phase.

5. The biosensor arrangement of claim 1, wherein the capacity value of the reference capacitor is selected so as to equate to a highest-possible capacity value of the sensor capacitors, wherein the capacity values of the sensor capacitors will be reduced by reactions occurring in the biological material during use.

* * * * *